(12) United States Patent
Mizutani et al.

(10) Patent No.: US 9,677,879 B2
(45) Date of Patent: Jun. 13, 2017

(54) TIRE APPEARANCE INSPECTION APPARATUS AND METHOD

(75) Inventors: Akinobu Mizutani, Kodaira (JP);
Tomoyuki Kaneko, Kodaira (JP)

(73) Assignee: KABUSHIKI KAISHA BRIDGESTONE, Tokyo (JP)

( * ) Notice: Subject to any disclaimer, the term of this patent is extended or adjusted under 35 U.S.C. 154(b) by 1100 days.

(21) Appl. No.: 13/114,698

(22) Filed: May 24, 2011

(65) Prior Publication Data

US 2011/0288814 A1    Nov. 24, 2011

(30) Foreign Application Priority Data

May 24, 2010   (JP) .................................. 2010-118590

(51) Int. Cl.
*G06F 15/00* (2006.01)
*G01B 11/25* (2006.01)
(Continued)

(52) U.S. Cl.
CPC ....... *G01B 11/2522* (2013.01); *G01M 17/027* (2013.01); *G06T 7/344* (2017.01); *G06T 2207/30108* (2013.01)

(58) Field of Classification Search
CPC .............. G01N 21/88; G01N 21/8851; G01N 21/8803; G01N 21/8806; G01N 21/95; G01N 21/9515; G01N 21/956; G01N 21/954; G06T 7/004; G06T 7/0042; G06T 7/0044; G06T 7/0046; G06T 7/0048; G06T 7/0051; G06T 7/0057; G06T 7/0067; G06T 7/0032; G06T 7/0022; G06T 7/0024; G06T 7/0026; G06T 7/0028; G06T 2207/30108;
(Continued)

(56) References Cited

U.S. PATENT DOCUMENTS 3,911,257 A * 10/1975 Whitehouse et al. ........ 702/168
3,918,816 A * 11/1975 Foster et al. .................. 356/602
(Continued)

FOREIGN PATENT DOCUMENTS

DE    10 2006 015 627 A1    10/2007
EP         0 565 320 A2 *    2/1993    .............. G01M 1/02
(Continued)

OTHER PUBLICATIONS

Kimball, Smoothing data with Fourier transforms, Mar.-Apr. 1974, Agronomy Journal, vol. 66, pp. 259-262.*
(Continued)

*Primary Examiner* — Regis Betsch
*Assistant Examiner* — Lisa Peters
(74) *Attorney, Agent, or Firm* — Oliff PLC (57) ABSTRACT

A tire appearance inspection apparatus and method employing image processing is capable of performing tire appearance inspection with great accuracy. The tire appearance inspection apparatus includes a sectional shape acquiring device for acquiring cross-sectional shapes of a tire in the radial direction along the circumference of the tire, an arc fitting device for fitting an arc to each of the cross-sectional shapes, an arc center position calculating device for calculating the center positions of the arcs, and a sectional shape aligning device for aligning the cross-sectional shapes using the center positions of the arcs for the cross-sectional shapes.

9 Claims, 8 Drawing Sheets

(51) Int. Cl.
  *G01M 17/02* (2006.01)
  *G06T 7/33* (2017.01)
(58) Field of Classification Search
  CPC . G01B 11/24; G01B 11/2408; G01B 11/2522; G01B 11/2504; G01M 17/027
  USPC .................. 702/150; 382/141, 149; 356/601; 731/146; 700/109, 110
  See application file for complete search history.

(56) References Cited

U.S. PATENT DOCUMENTS

| | | | | |
|---|---|---|---|---|
| 5,619,587 | A * | 4/1997 | Willoughby et al. | 382/141 |
| 6,615,144 | B2 * | 9/2003 | Williams | G05B 13/026 702/142 |
| 6,840,097 | B1 * | 1/2005 | Huber | G01B 11/30 356/237.1 |
| 7,199,880 | B2 * | 4/2007 | Braghiroli | 356/601 |
| 7,805,987 | B1 * | 10/2010 | Smith | G01M 17/027 73/146.5 |
| 2001/0024279 | A1 | 9/2001 | Kaneko et al. | |
| 2013/0120566 | A1 * | 5/2013 | Fujii et al. | 348/135 |

FOREIGN PATENT DOCUMENTS

| | | |
|---|---|---|
| EP | 0 565 320 A2 | 10/1993 |
| JP | A-2-105007 | 4/1990 |
| JP | A-2001-249012 | 9/2001 |
| JP | A-2007-263692 | 10/2007 |

OTHER PUBLICATIONS

Graham, MEP Pupil Text 1-6, Nov. 2004, CIMT, University of Plymouth, Chapter 3, Section 8, pp. 96-98.*
Gautschy, Curve Fitting with Fourier Transform, Dec. 1982, International Amateur-Professional Photoelectric Photometry Communication, No. 10, p. 11.*
Sep. 21, 2011 Search Report issued for European Application No. 11250543.3.

* cited by examiner

TIRE APPEARANCE INSPECTION APPARATUS AND METHOD

CROSS-REFERENCE TO RELATED APPLICATION

This application is based on and claims the benefit of priority from Japanese Patent Application No. 2010-118590, filed in Japan on May 24, 2010, the content of which is incorporated herein by reference.

BACKGROUND OF THE INVENTION

1. Field of the Invention

The present invention relates to an apparatus and method for inspecting the appearance of tires. In particular, the invention relates to a tire appearance inspection apparatus and method in which tire appearance is inspected by performing an image processing on captured images of the appearance of a tire.

2. Description of the Related Art

A conventionally known tire appearance inspection apparatus captures images of the tire surface with an image capturing device and determines acceptance or rejection of the tire through an image processing on them by an image processing device, by which defects (defective spots) made in the tire building process are detected.

The image capturing device of a tire appearance inspection apparatus may consist of a rotating table for rotating a tire to be inspected, a plurality of illuminators for shining a slit light on the tire surface, such as the inside surface of the tire, and a plurality of cameras for capturing the images of the tire surface illuminated by the slit light. The illuminators may employ red laser, and the cameras used may be CCD area cameras. The images of the inside surface of the tire are thus captured using a technique called the light-section method. The captured images shot by the plurality of cameras and obtained as sectional shapes of the tire inside surface are outputted successively to an image processing device connected to the cameras. The image processing device produces an inspection image by combining the captured images of the tire inside surface for the whole circumference of the tire and performs necessary image processing on the inspection image. In this manner, the tire appearance inspection apparatus inspects the tire surface for defective spots, thereby determining acceptance or rejection of the tire. For example, the tire surface is inspected for the presence or absence of defects by checking changes in the gradient of luminance of pixels constituting the captured images or comparing height information present in the pixels against threshold values.

For a successful inspection of the inside surface of a tire, however, it is prerequisite that the inspection image is obtained in advance with high accuracy. If, for instance, a stationary camera captures the inside surface of a tire rotating with its center out of alignment with the rotation center of the rotating table, then the distance to the inside surface of the tire shot by the camera changes with the rotation of the tire. This will result in the captured images of the cross-sectional shapes having positional shifts, or differences, in the tire radial direction. Hence, it is necessary to align the captured images if an accurate inspection image is to be obtained.

As a way to align captured images, all the captured images may be aligned uniformly, using the captured image with the closest distance between the camera and the tire inside surface for reference. In this case, however, there may be cases where defects in the radial height of the tire, even if they exist, are also removed by the alignment. Otherwise, it may be possible that the trouble is taken to capture the images for the second time by repositioning the tire to align the rotation center of the rotating table with the tire center. But such a procedure is of course detrimental to inspection efficiency. Therefore, if the inspection efficiency is to be enhanced, it is considered necessary to automatically eliminate by image processing the effects of such eccentricity, or nonalignment of the rotation center of the rotating table with the tire center, when producing an inspection image from the captured images.

The present invention has been made to solve the above-described problem, and an object thereof is to provide a tire appearance inspection apparatus and method that utilizes image processing in accomplishing tire appearance inspections with high accuracy.

SUMMARY OF THE INVENTION

In one aspect of the present invention, a tire appearance inspection apparatus includes a sectional shape acquiring device configured to acquire cross-sectional shapes of a tire in the tire radial direction along the circumference of the tire, an arc fitting device configured to fit an arc to each of the cross-sectional shapes, an arc center position calculating device configured to calculate a center position of each of the arcs, and a sectional shape aligning device configured to align the cross-sectional shapes with respect to the center positions of the arcs for the cross-sectional shapes.

According to this aspect of the invention, the cross-sectional shapes of a tire can be aligned with respect to the center positions of the arcs.

In another aspect of the present invention, a tire appearance inspection method includes the steps of acquiring cross-sectional shapes of a tire in the tire radial direction along the circumference of the tire by a sectional shape acquiring device, fitting an arc in a region containing an extremal value on each cross-sectional shape corresponding to a sidewall of the tire by an arc fitting device, calculating a center position of each of the arcs by an arc center position calculating device, and aligning the cross-sectional shapes with respect to the center positions of the arcs of the cross-sectional shapes by a sectional shape aligning device.

According to this aspect of the invention, the arc can be fitted easily because the position of the extremal value corresponding to the sidewall of the tire has substantially the same shape for all the cross-sectional shapes, and besides it is possible to align the cross-sectional shapes with accuracy with respect to the center positions of the arcs.

DESCRIPTION OF PREFERRED EMBODIMENTS

The invention will now be described based on preferred embodiments which do not intend to limit the scope of the present invention but exemplify the invention. All of the features and the combinations thereof described in the embodiments are not necessarily essential to the invention, but include arrangements and combinations thereof that can be employed selectively.

Figure 1:
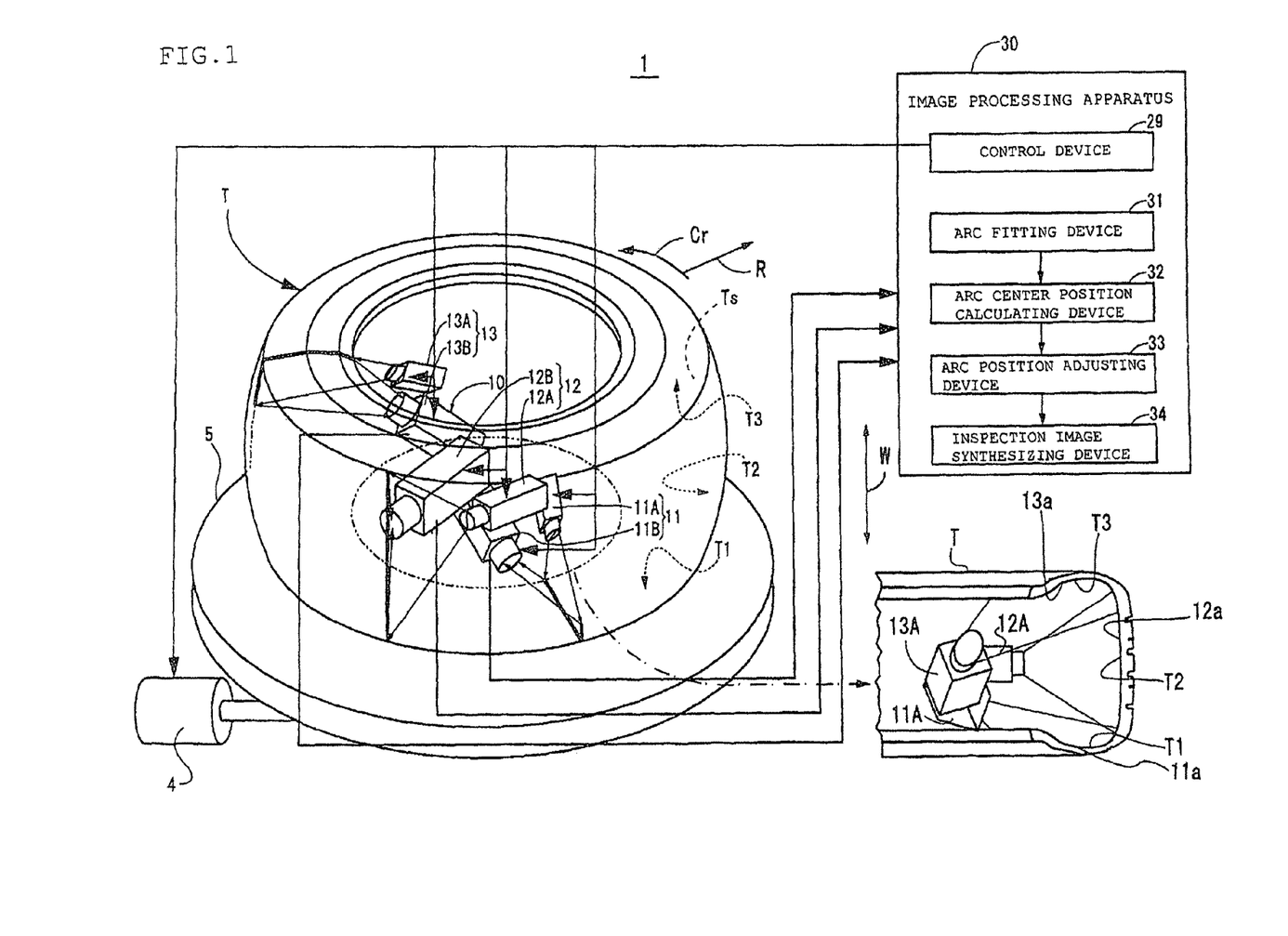
FIG. 1 is an overall schematic diagram of a tire appearance inspection apparatus in accordance with an embodiment of the present invention.
Figure 2:
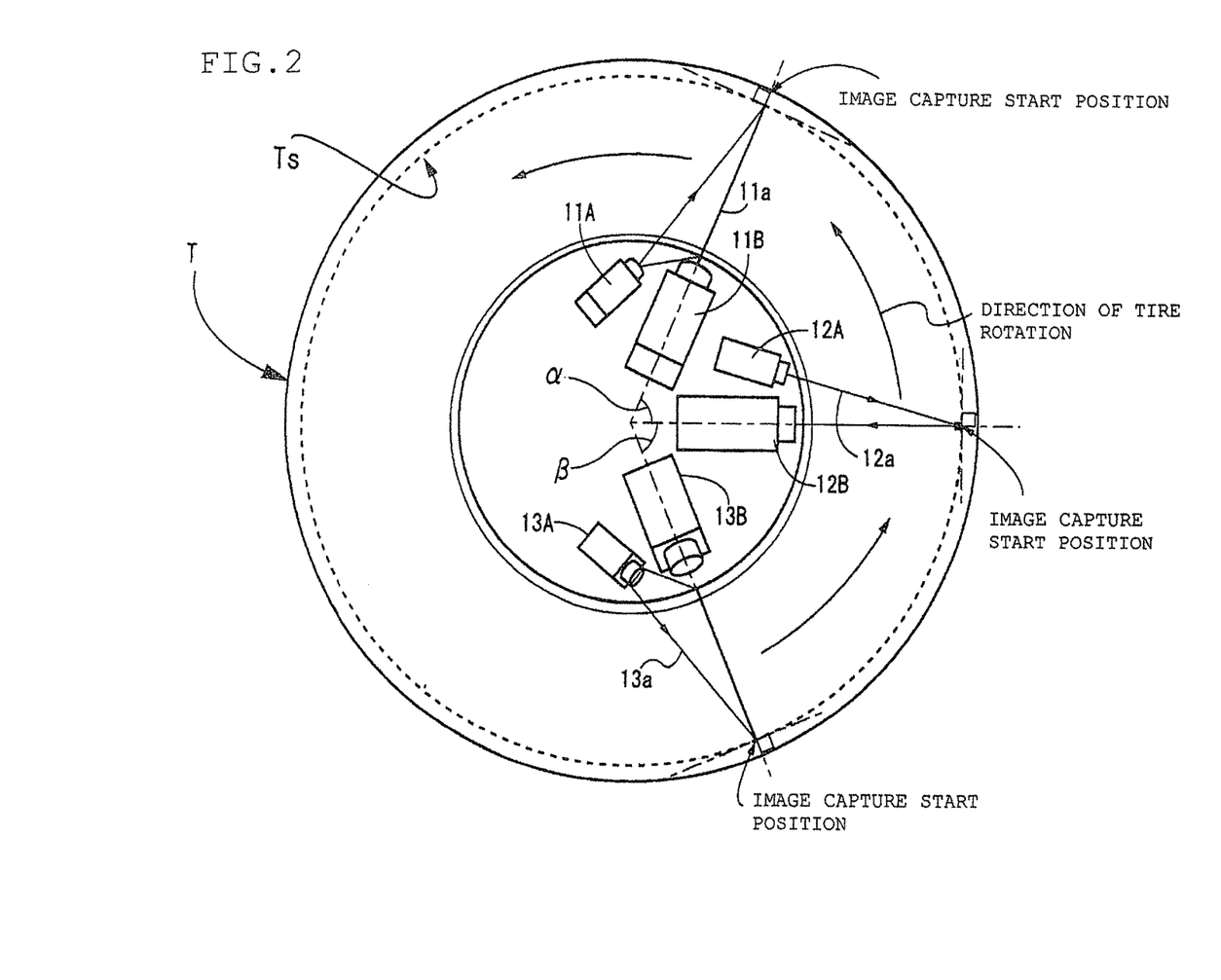
FIG. 2 is an arrangement plan of camera sets in relation to a tire in accordance with an embodiment of the present invention.

FIG. 1 is an overall schematic diagram showing a tire appearance inspection apparatus 1, and FIG. 2 is an arrangement plan of camera sets 11 to 13 in relation to a tire T. Hereinbelow, the tire appearance inspection apparatus is explained referring to FIG. 1 and FIG. 2. As illustrated in FIG. 1, the tire appearance inspection apparatus 1 is constituted roughly of an image capturing apparatus 10, as a sectional shape acquiring device for capturing the images of tire surface, and an image processing apparatus 30.

The image capturing apparatus 10 is formed of a rotating table 5, on which the tire T is placed as an object to be inspected, and camera sets 11 to 13, which capture images of the respective regions of a tire inside surface Ts.

The rotating table 5 is rotated driven by a motor 4, which is built in the not-shown swivel base of the table, thereby turning the tire T placed on its side. The motor 4, which is connected to the image processing apparatus 30 to be discussed later, runs according to the signals outputted from a control device 29 of the image processing apparatus 30.

The camera sets 11 to 13 are positioned within the inner opening area of the tire such that they are dislocated from each other by angle α or angle β in the circumferential direction Cr of the tire. They comprise an illuminator 11A and a camera 118, an illuminator 12A and a camera 12B, and an illuminator 13A and a camera 13B. Each of the illuminators 11A to 13A, which casts a slit light of red laser, for instance, is disposed such that the direction of extension of the slit is the axial (width) direction W of the tire. The cameras 11B to 138 are constituted by CCD cameras, for instance, and the images of illuminated portions 11a, 12a, and 13a by slit light from the illuminators 11A to 13A are captured by the cameras corresponding thereto. The camera set 11 captures the image of lower tire side T1, the camera set 12 the image of tire crown T2, and the camera set 13 the image of upper tire side T3. That is, the images are taken with the tire inside surface Ts, which is the area to be inspected, divided into three regions. It is to be noted also that the camera sets 11 to 13 capture the images of their respective regions of the tire inside surface Ts with some overlaps with each other.

More specifically, the illuminator 11A of the camera set 11 casts a slit light in the radial direction R and the axial direction W of the Lire to shine an extent covering the tire side T1 and part of the tire crown T2; the illuminator 12A of the camera set 12 casts a slit light onto the tire crown T2 in the axial direction W; and the illuminator 13A of the camera set 13 casts a slit light in the radial direction R and the axial direction W of the tire to shine an extent covering the tire side T3 and part of the tire crown T2. In other words, the camera set 11 captures the image of the tire side T1, which is a side of the tire inside surface Ts closer to the rotating table 5, the camera set 12 captures the image of the tire crown T2, and the camera set 13 captures the image of the tire side T3, which is the other side of the tire inside surface Ts.

It may be understood that the angle α and the angle β by which the camera sets 11 to 13 are circumferentially dislocated from each other may be determined as appropriate provided the camera sets 11 to 13 disposed within the inner opening area of the tire T can accomplish image capturing of the tire inside surface Ts.

Also, the camera sets 11 to 13 are connected to the image processing apparatus 30, and the casting of the slit light by the illuminators 11A to 13A and the image capturing by the cameras 11B to 13B are controlled by the control device 29.

Sectional images P1*, P2*, and P3* of the tire cross section in the radial direction to be captured by the cameras 11B to 13B are outputted successively to the image processing apparatus 30, which is connected with each of the cameras 11B to 13B. The sectional images P1*, P2*, and P3* to be captured by the cameras 11B to 13B are obtained with the tire inside surface Ts divided, for instance, into 10,000 parts in the circumferential direction Cr. Thus, cross-sectional shapes in the radial direction R of the tire inside surface Ts are captured in the sectional images P1*, P2*, and P3* (see FIG. 3).

Figure 4:
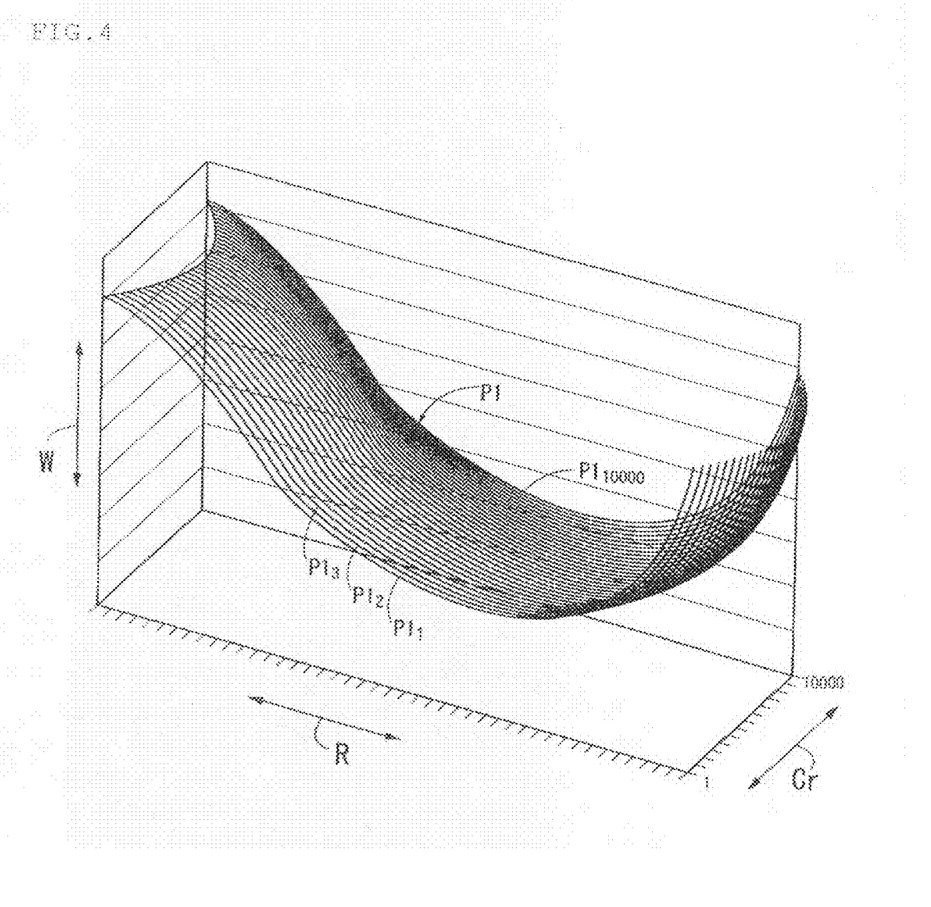
FIG. 4 shows a captured image having positional shifts due to eccentricity in accordance with an embodiment of the present invention.

FIG. 4 is a diagram showing the sectional shapes f in sectional images $P1_1$, $P1_2$, $P1_3$, ..., $P1_{10000}$ plotted on the coordinate system of the camera 11B.

Figure 3:
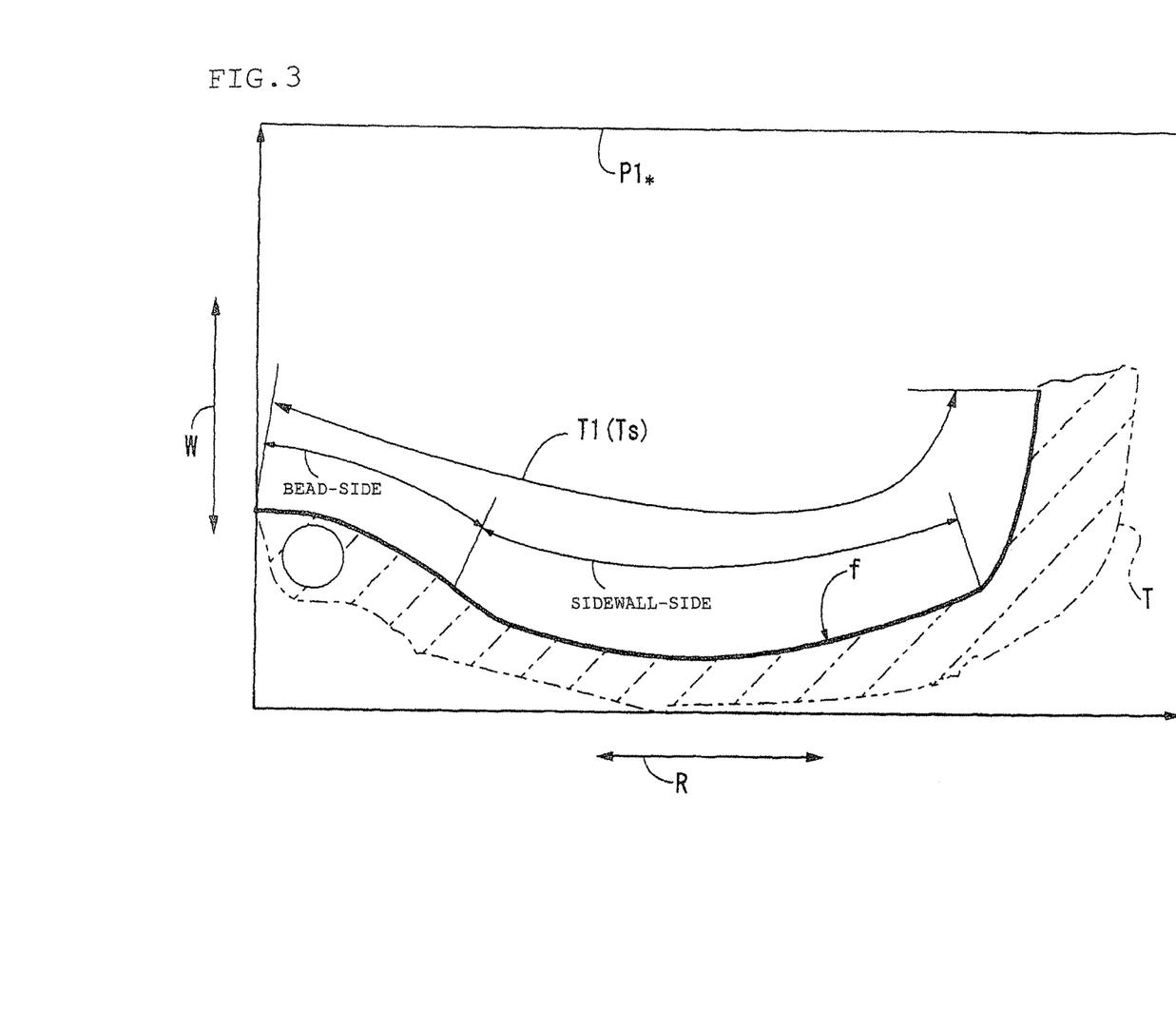
FIG. 3 is a conceptual diagram showing a cross-sectional shape captured in a sectional image in accordance with an embodiment of the present invention.

For example, a sectional shape f of the tire inside surface Ts as shown in FIG. 3 is obtained in the sectional image P1* captured by the camera 11B. It is to be noted that the solid line in FIG. 3 shows a sectional shape f that is actually captured when the slit light is cast, and the two-dot chain line is a virtual line showing the outer shape of the tire cross section.

As shown in FIG. 4, the sectional images $P1_1$, $P1_2$, $P1_3$, ..., $P1_{10000}$, which constitute a captured image P1, are obtained as the captured image P1 for the whole circumference of the tire, linearly arranged side by side with respect to the shooting position of the camera 11B. That is, the eccentricity of the tire T relative to the rotating table 5 is captured as positional shifts in the radial direction R in the sectional images P1*.

Also, although not shown, a captured image 22 of the tire crown T2 to be shot by the camera 12B are constituted by sectional images $P2_1$, $P2_2$, $P2_3$, ..., $P2_{10000}$, and a captured image P3 of the tire side T3 to be shot by the camera 13B are constituted by sectional images $P3_1$, $P3_2$, $P3_3$, ..., $P3_{10000}$.

Note that the camera 11B is disposed with its optical axis facing downward by angle γ in relation to the optical axis of the camera 12B, which is horizontal, and, as shown in FIG. 3, a sectional shape f is obtained on the coordinate system relative to the tire mounting surface of the rotating table 5.

The image processing apparatus 30 is what is called a computer, thus having CPU as a computing device, ROM and RAM as a storage device, and input-output interface as a communication device. The image processing apparatus 30 includes a control device 29, an arc fitting device 31, an arc center position calculating device 32, an arc center position adjusting device 33, and an inspection image synthesizing device 34. It should be noted that, in a preferred embodiment, the image processing by the arc fitting device 31, the arc center position calculating device 32, and the arc center position adjusting device 33 is performed on the sectional images P1* only, out of the sectional images P1*, P2*, and P3*.

The control device 29 controls the image capturing of the tire inside surface Ts by outputting an image capturing start signal and an image capturing end signal to the camera sets 11 to 13 and the motor 4.

Figure 5:
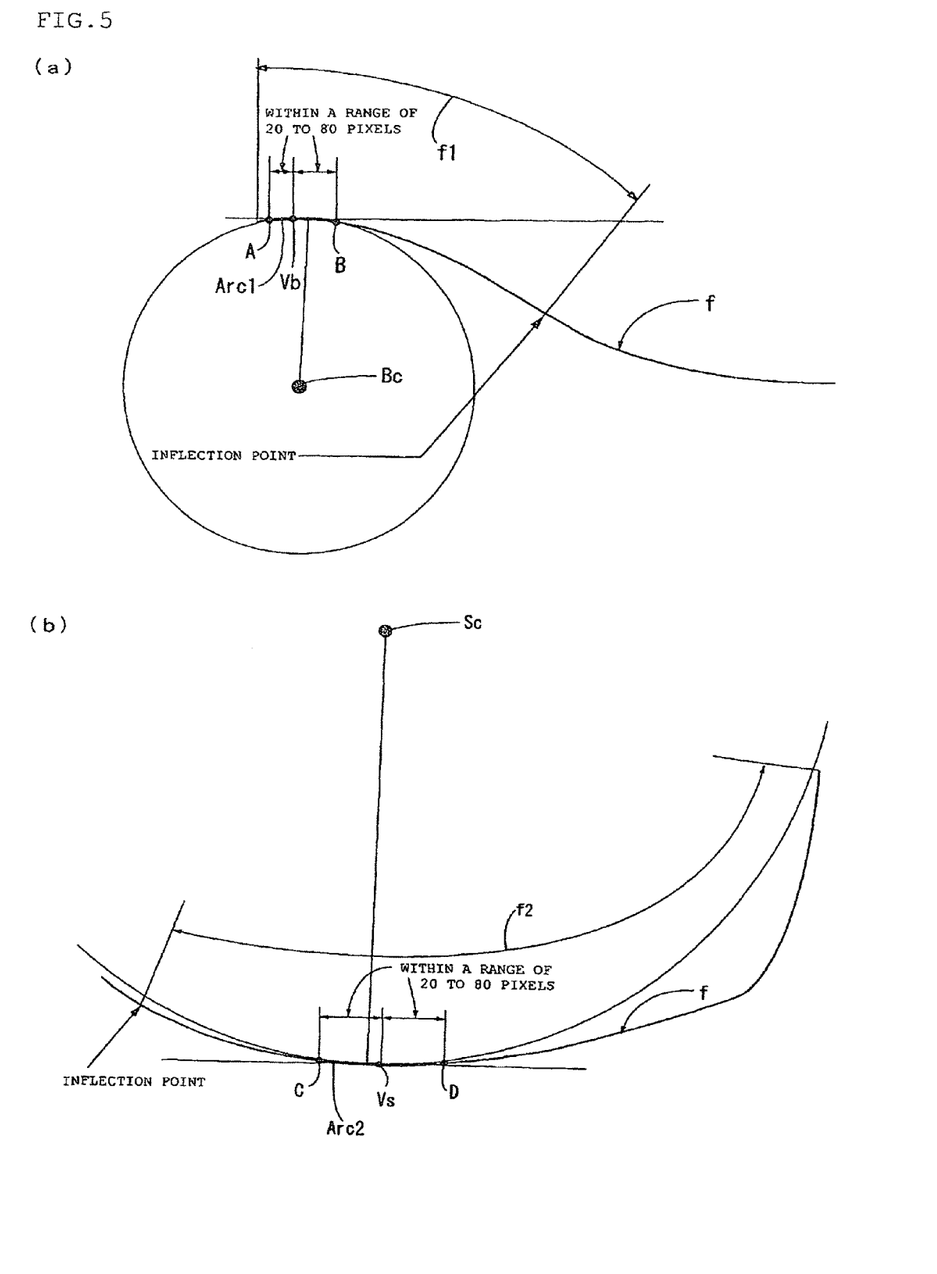
FIG. 5 is a conceptual diagram for setting a bead-side arc and a sidewall-side arc in accordance with an embodiment of the present invention.

The arc fitting device 31 sets extremal values Vb and Vs with reference to the change in the coordinate positions of pixels constituting the sectional shape f of each of the sectional images P1*. The bead-side extremal value Vb and the sidewall-side extremal value Vs are set at the point where the slope of the tangent line changes from decrease to increase or from increase to decrease. Further, the arc fitting device 31 sets a bead-side arc Arc1 using at least three points, which are the bead-side extremal value Vb and two other points, one on each side of the bead-side extremal value Vb. Also, the arc fitting device 31 sets a sidewall-side arc Arc2 using at least three points, which are the sidewall-side extremal value Vs and two other points, one on each side of the sidewall-side extremal value Vs.

The sectional shape f on the tire side T1 consists in a curve connecting curve f1, which swells out upward near the bead, and curve f2, which swells out downward along the sidewall. The position where the upward-swelling curve f1 near the bead is connected to the downward-swelling curve f2 along the sidewall is the inflection point on the sectional shape f.

In other words, the arc fitting device 31 sets a bead-side arc Arc1 along the curvature of the upward-swelling curve f1 near the bead and a sidewall-side arc Arc2 along the curvature of the downward-swelling curve f2 along the sidewall. It is to be noted that the bead-side arc Arc1 and the sidewall-side arc Arc2 do not have to be inscribed arcs at curves f1 and f2, respectively.

As shown in FIG. 5A, the bead-side arc Arc1 is set by calculating an arc that has arc point A, bead-side extremal value Vb, and arc point B thereon. That is, from the sectional shape f of the sectional image P1*, represented in an orientation of the tire placed on the rotating table 5, the bead-side extremal value Vb is extracted from the upward-swelling curve f1 near the bead, the arc point A is selected from the positions 20 to 80 pixels on the curve f1 leftward from the bead-side extremal value Vb, and the arc point B is selected from the positions 20 to 80 pixels on the curve f1 rightward from the bead-side extremal value Vb. The bead-side extremal value Vb is extracted as the position where a straight line parallel to the coordinate axis in the radial direction R, when moved up or down, touches the upward-swelling curve f1 near the bead.

Note that the bead-side extremal value Vb may also be extracted as the point where a straight line connecting the inflection point of the sectional shape f and the bead-side end point thereof, when parallelly moved, touches the curve f1 of the sectional shape f. By doing so, it is possible to set the bead-side extremal value Vb without regard to the type of tire.

Also, as shown in FIG. 5B, the sidewall-side arc Arc2 is set by calculating an arc that has arc point C, sidewall-side extremal value Vs, and arc point D thereon. That is, from the sectional shape f of the sectional image P1*, represented in an orientation of the tire placed on the rotating table 5, the sidewall-side extremal value Vs is extracted from the downward-swelling curve 12 along the sidewall, the arc point C is selected from the positions 20 to 80 pixels on the curve f2 leftward from the sidewall-side extremal value Vs, and the arc point D is selected from the positions 20 to 80 pixels on the curve f2 rightward from the sidewall-side extremal value Vs. The sidewall-side extremal value Vs is extracted as the position where a straight line parallel to the coordinate axis in the radial direction R, when moved up or down, touches the curve f2 along the sidewall. It should be appreciated that the position of the sidewall-side extremal value Vs corresponds to the maximum width point of the tire.

There is a reason for setting the range of 20 to 80 pixels apart from the bead-side extremal value Vb and the sidewall-side extremal value Vs, respectively, on each side thereof from which the arc point A and the arc point B and the arc point C and the arc point D, respectively, are selected. There are innumerable points on the curve f1 which runs past the bead-side extremal value Vb and extends on both sides thereof, and likewise there are innumerable points on the curve f2 which runs past the sidewall-side extremal value Vs and extends on both sides thereof. Yet, it is necessary to set arcs of approximately the same size in the sectional images $P1_1, P1_2, P1_3, \ldots, P1_{10000}$. Thus, selection of the arc points A and B and the arc points C and D in the range of 20 to 80 pixels apart from the extremal values Vb and Vs, respectively, allows the setting of reliable arcs Arc1 and Arc2 in each of the sectional images $P1_1, P1_2, P1_3, \ldots, P1_{10000}$.

An approach may be conceivable, in which the arcs Arc1 and Arc2 are set by calculating approximate curves from a multiplicity of points near the extremal value Vb and Vs on the sectional shape f, but such an approach is not preferable since it may suffer from lowered inspection efficiency. The use of a multiplicity of points may result in setting arcs of extremely different sizes due to noise in the sectional images, which is defective unevenness of tire surface and the like. Thus, arc points A to D are set from within the above-mentioned ranges.

As described above, the arc fitting device 31 sets the bead-side arc Arc1 and the sidewall-side arc Arc2 in such a manner that they are respectively in contact with the curve (contour) f1 and the curve (contour) f2 in the bead-sidewall region of the sectional shape f in each of the sectional images P1*. It should be noted that the bead-side arc Arc1 and the sidewall-side arc Arc2 in the bead-sidewall region are set on opposite sides to each other with the sectional shape f in between.

Also, as previously discussed, the arcs Arc1 and Arc2 are set using three points each on the curve f1 and the curve f2 of the sectional shape f. However, the arrangement may also be such that the arcs Arc1 and Arc2 are set using more than three points each on the curve f1 and the curve f2.

The arc fitting device 31 fits the arc in a region containing an extremal value at a position on the cross-sectional shape corresponding to the sidewall of the tire so that each of cross-sectional shape may be aligned with accuracy.

Since the position of the extremal value corresponding to the sidewall of the tire has substantially the same shape for all the cross-sectional shapes in the sectional images P1*, the arc corresponding with the position of extremal value may be fitted. Thereby, the cross-sectional shapes with accuracy with respect to the center positions of the arcs in the sectional images P1* may be aligned with accuracy.

Note that the extremal value substantially coincides with the position of maximum width of tire inside surface.

Further, since the arc fitting device 31 fits the arc in accordance with a plurality of extremal values on the cross-sectional shape by the extremal value, a plurality of standards when each of cross-sectional shape is aligned may be set in each of cross-sectional shape. Thereby, each of cross-sectional shape may be aligned with higher accuracy.

The arc center position calculating device 32 calculates the center positions of the two arcs Arc1 and Arc2, respectively, set by the arc fitting device 31 for each of the sectional images P1*. In other words, the arc center position calculating device 32 calculates the center position Bc of a circle containing the bead-side arc Arc1 that passes through the bead-side extremal value Vb, the arc point A, and the arc point B, and also calculates the center position Sc of a circle containing the sidewall-side arc Arc2 that passes through the sidewall-side extremal value Vs, the arc point C, and the arc point D.

It is easy to calculate the center positions Bc and Sc. For example, the center position Bc of the bead-side arc Arc1 is the intersection of the normal line from the midpoint of the line segment connecting the arc point A and the bead-side extremal value Vb and the normal line from the midpoint of the line segment connecting the bead-side extremal value Vb and the arc point B. Similarly, the center position Sc of the sidewall-side arc Arc2 is the intersection of the normal line from the midpoint of the line segment connecting the arc point C and the sidewall-side extremal value Vs and the normal line from the midpoint of the line segment connecting the sidewall-side extremal value Vs and the arc point D.

The arc center position adjusting device 33 calculates a bead-side center curve Hb, which is an approximate curve, by performing a Fourier transform on the broken (sequential) line of the line segments connecting the center positions Bc of the bead-side arc Arc1 in the sectional images P1* first and then a sidewall-side center curve Hs, which is an approximate curve, by performing a Fourier transform on the broken line of the line segments connecting the center positions Sc of the sidewall-side arc Arc2 in the sectional images P1*. The calculated bead-side center curve Hb and sidewall-side center curve Hs represent ones with the secondary and subsequent components in the Fourier transform excluded.

The arc center position calculating device 32, which is means for aligning the cross-sectional shape, and the arc center position adjusting device 33 perform alignment such that the center positions of the cross-sectional shapes are positioned on a curve obtained by a Fourier transform on a line connecting the center positions of the arcs having been fitted to the same position on the cross-sectional shapes. And then the broken line is calculated as a curve by the Fourier transform on the line connecting center positions of a plurality of arcs. Thereby, the alignment in response to the eccentricity of a rotating tire can be accomplished.

Figure 6:
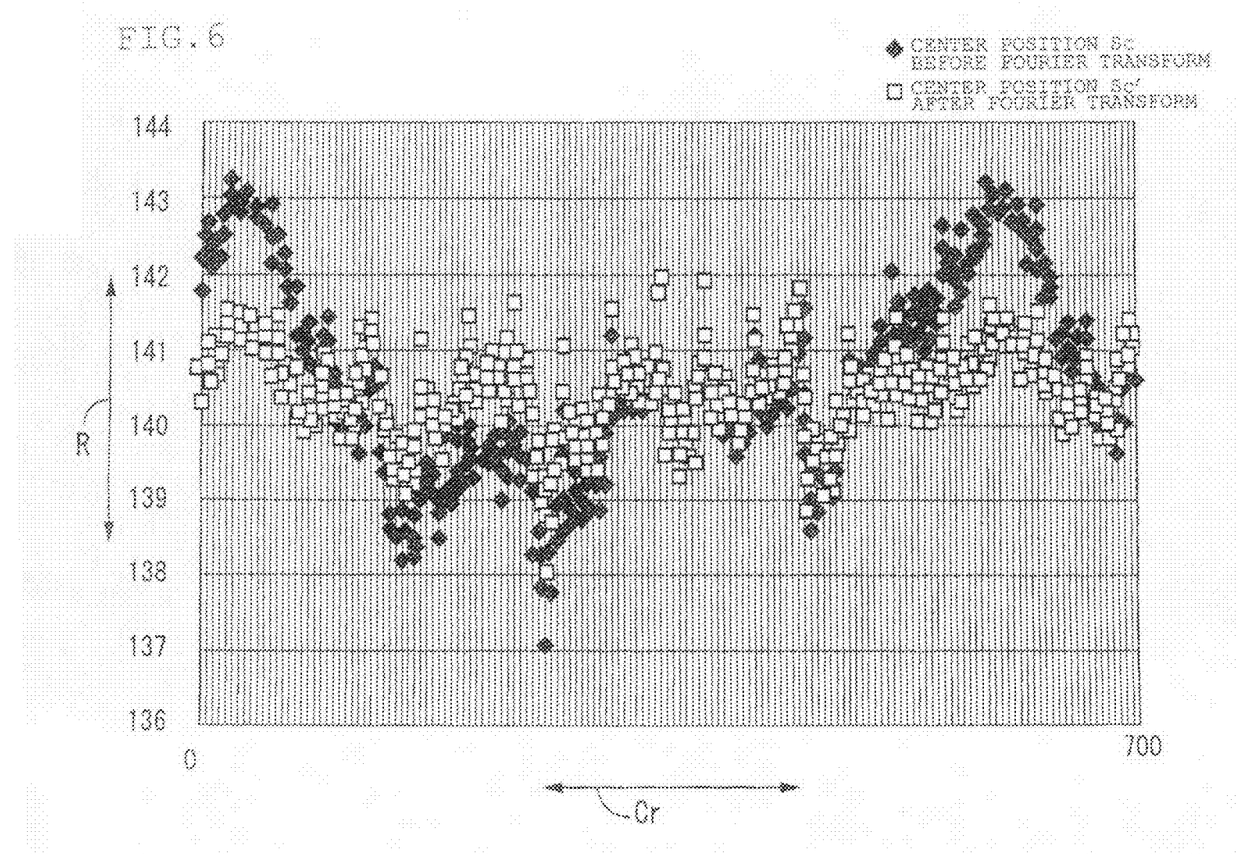
FIG. 6 is a scatter diagram plotting the center positions of the sidewall-side arcs before and after a Fourier transform in accordance with an embodiment of the present invention.

FIG. 6 is a scatter diagram plotting the center positions Sc of the sidewall-side arcs Arc2 in the sectional images P1* as calculated by the arc center position calculating device 32 and the center positions Sc' of the sidewall-side arcs Arc2 as calculated by the arc center position adjusting device 33.

Figure 8:
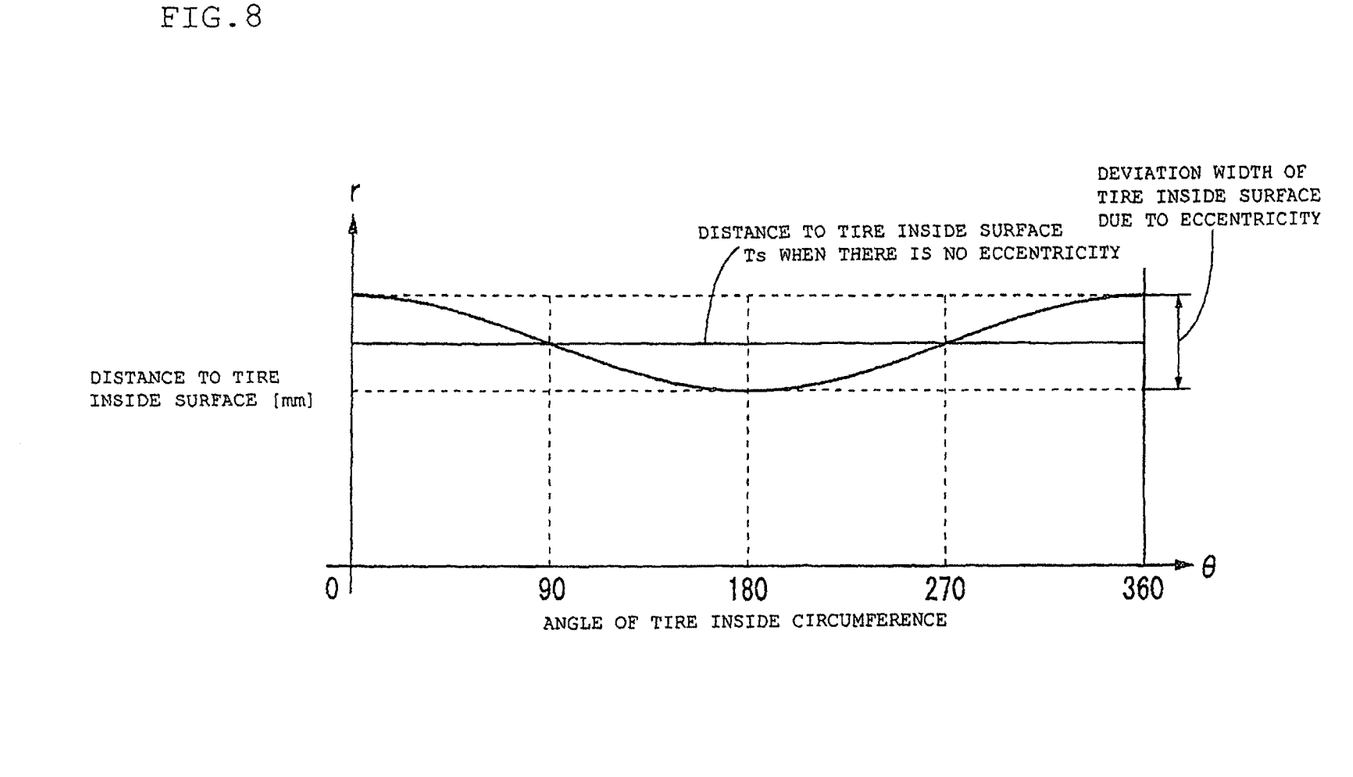
FIG. 8 is a conceptual diagram showing a relationship between a bead-side center curve and a sidewall-side center curve and the distance from the camera to the tire surface in accordance with an embodiment of the present invention.

As shown in FIG. 6, the center positions Sc of the sidewall-side arcs Arc2 as calculated by the arc center position calculating device 32 have considerable variation cyclically in the radial direction R, whereas the center positions Sc' having been subjected to a Fourier transform present a cyclical scatter plot narrower in variation width in the radial direction R than the center positions Sc, the latter centering around the intermediate values of variation of the center positions Sc in the radial direction R. This is because the changes in the distance from the cameras 11B to 13B to the tire inside surface Ts can be represented sinusoidally, as shown in FIG. 8, when the images are taken with the center of the tire placed eccentrically (with positional shift) in relation to the rotation center of the rotating table 5.

Accordingly, a Fourier transform on the broken line connecting the arc center positions Bc and Sc as calculated by the arc center position calculating device 32a can accomplish a close enough approximation to the sinusoidal wave which represents the changes in distance to the tire inside surface Ts. In particular, the difference in the radial direction R due to the eccentricity in each of the sectional images P1* can be corrected by employing the primary components of the Fourier transform only and discarding the secondary and subsequent components.

Following this, the arc center position adjusting device 33 aligns the sectional images P1* using bead-side center curve Hb and sidewall-side center curve Hs. More specifically, the center position Bc of the bead-side arc Arc1 in each of the sectional images P1* is placed on the bead-side center curve Hb, and the center position Sc of the sidewall-side arc Arc2 in each of the sectional images P1* is placed on the sidewall-side center curve Hs.

Figure 7:
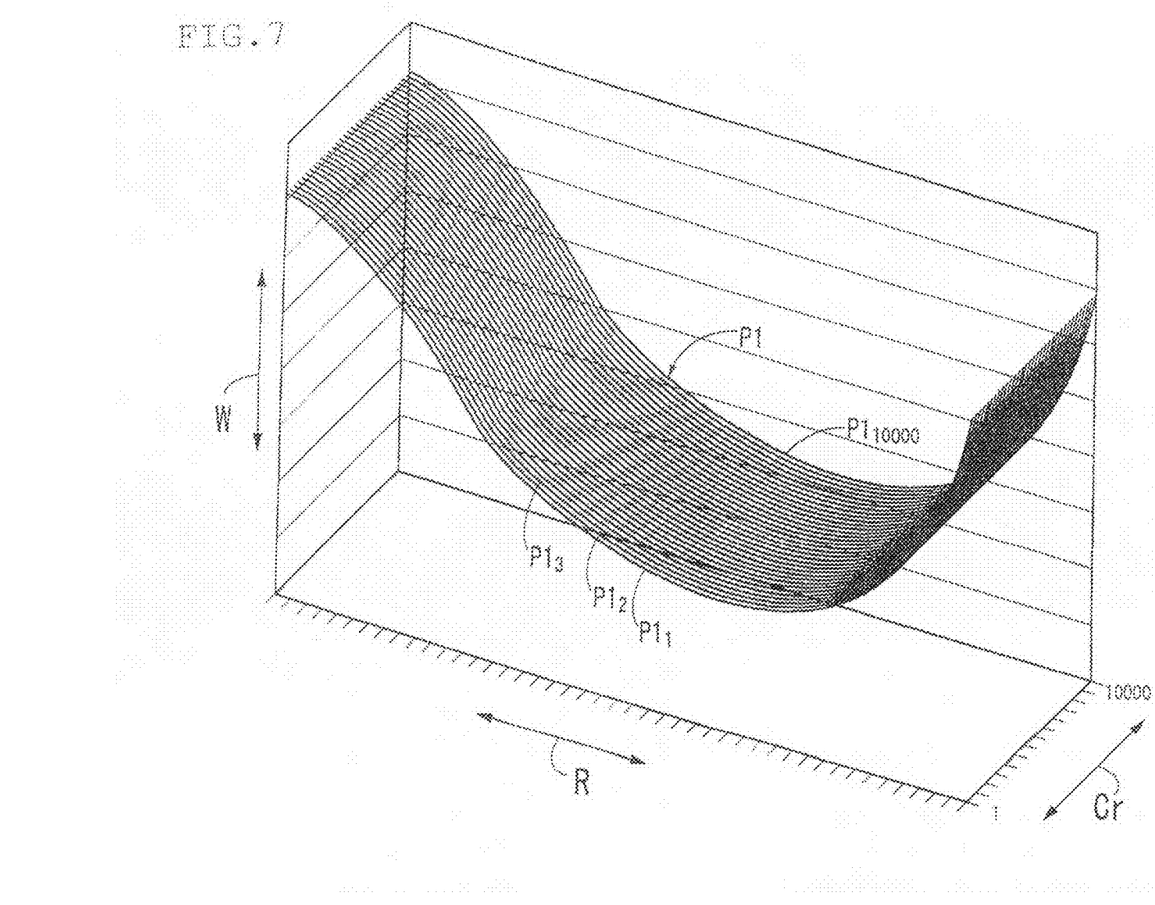
FIG. 7 shows a captured image aligned in accordance with an embodiment of the present invention.

As a result, the sectional images $P1_1$, $P1_2$, $P1_3$, . . . , $P1_{10000}$ are aligned with each other as shown in FIG. 7. That is, they are aligned in a coordinate system unifying the respective coordinates of the sectional images P1*.

It should be understood by those skilled in the art that it is not permissible to align the sectional images $P1_1$, $P1_2$, $P1_3$, . . . , $P1_{10000}$ uniformly in the radial direction. The reason is that such an alignment may result in a uniform alignment even when the tire is actually an eccentrically-molded one. Should such an arrangement be used, the defects, if any, maybe concealed by the image processing even on tires which have been molded with eccentricity relative to the tire center.

The inspection image synthesizing device 34 obtains an inspection image through the following process. Firstly, a captured image P1 is produced by combining the aligned sectional images P1*. Then, after correcting the positional difference in the circumferential direction between the captured image P1 and the captured image P2 resulting from the camera positions, the captured image P1 and the captured image P2 are combined with each other. Finally, after correcting the positional difference in the circumferential direction between the captured image 22 and the captured image P3 resulting from the camera positions, a single inspection image is produced by synthesizing the captured image 3 with the captured image 22 having been synthesized with the captured image P1.

The inspection image synthesized by the inspection image synthesizing device 34 is outputted to a subsequent inspection device which performs its image processing.

Examples of such inspection devices include stain detecting devices which detect stains or dirt based on the changes in luminance of pixels constituting an inspection image and defect detecting devices which inspect for the presence of defects or the eccentricity of tires based on the unevenness information of the tire inside surface in the inspection images obtained by light-section method.

Now a description will be given of an inspection method using the tire appearance inspection apparatus 1.

Firstly, the inspector places a tire T, which is an object to be inspected, on its side on the rotating table 5. At this time, it is not necessary that the rotation center of the rotating table 5 is exactly in alignment with the tire center.

Next, the camera sets 11 to 13 are positioned within the inner opening area of the tire T, and an inspection start signal is outputted from a not-shown input device to the image processing apparatus 30.

The control device 29 of the image processing apparatus 30 outputs an image capture start signal to the camera sets 11 to 13 and a rotation start signal for the rotating table 5 to the motor 4. The speed of the motor 4 and the frequency of image capturing by the camera sets 11 to 13 are controlled by the control device 29 to ensure synchronism such that the whole circumference of the tire is covered by 10,000 times of image capturing of the tire inside surface Ts by the camera sets 11 to 13. The sectional images P1*, P2*, and P3* are successively outputted from the camera sets 11 to 13 to the image processing apparatus 30.

On completion of all the image capturing, the arc fitting device 31 of the image processing apparatus 30 performs an image processing on the sectional images P1*, out of the sectional images P1*, P2*, and P3*. More specifically, the extremal values Vb and Vs are extracted from the sectional shape f in each of the sectional images P1*.

Next, two pixels, one pixel each from the range of 20 to 80 pixels on each side of the bead-side extremal value Vb on the curve f1, are extracted as arc points A and B, and then a bead-side arc Arc1, which passes through the arc points A and B and the bead-side extremal value Vb, is set. Similarly, two pixels, one pixel each from the range of 20 to 80 pixels on each side of the sidewall-side extremal value Vs on the curve f2, are extracted as arc points C and D, and then a sidewall-side arc Arc2, which passes through the arc points C and D and the sidewall-side extremal value Vs, is set. The Arc1 and Arc2 are outputted to the arc center position calculating device 32.

Following this, the arc center position calculating device 32 calculates the center positions Bc and Sc of circles containing the arcs Arc1 and Arc2, respectively.

A broken line connecting the center positions Bc in the respective sectional images P1* and a broken line connecting the center positions Sc therein are prepared, and a bead-side center curve Hb and a sidewall-side center curve Hs are calculated by performing a Fourier transform on the respective broken lines. The bead-side center curve Hb and the sidewall-side center curve Hs are outputted to the arc center position adjusting device 33.

Then the arc center position adjusting device 33 aligns the sectional images P1* with each other, using the bead-side center curve Hb and the sidewall-side center curve Hs. That is, all the sectional images P1* are positionally shifted such that the center position Bc of the bead-side arc Arc1 in each of the sectional images P1* is placed on the bead-side center curve Hb, and then all the sectional images P1* are positionally shifted such that the center position Sc in each of the sectional images P1* is placed on the sidewall-side center curve Hs.

As a result, the sectional images P1* of the tire inside surface Ts which have been captured with some eccentricity present are aligned with each other as if they have been captured without any eccentricity. The sectional images P1* thus aligned are outputted to the inspection image synthesizing device 34.

The inspection image synthesizing device 34 combines the sectional images P1* into a captured image P1. Also, the inspection image synthesizing device 34 creates an inspection image by making corrections to the positional differences in the circumferential direction of the camera sets 11 to 13 in capturing the images of the tire inside surface Ts and then synthesizing the captured images P2 and P3 with the captured image P1.

The inspection image thus synthesized is outputted to a subsequent inspection device.

As described above, according to the tire appearance inspection apparatus 1 of the present invention, the sectional images P1* of the tire inside surface Ts can be automatically aligned with each other by eliminating eccentricity even when the tire is placed eccentrically on the rotating table 5. Hence, more accurate inspection of the tire by an inspection device in a subsequent inspection process can be carried out.

The alignment of the sectional images P1* as explained above is based on setting the bead-side arc Arc1 and the sidewall-side arc Arc2 using the bead-side extremal value Vb and the sidewall-side extremal value Vs and then calculating the center positions Bc and Sc of the arcs Arc1 and Arc2. However, the arrangement maybe such that the sectional images P1* are aligned with each other using the sidewall-side extremal value Vs only. This is because, depending on the type of tire T, there are cases where the curve f1, which swells out upward on the bead side, cannot be obtained. In such a case, the sectional images P1* may be aligned with each other using the sidewall-side extremal value Vs only. In this way, the sectional images P1* can be aligned with each other without regard to the type of tire.

Also, in the embodiment so far explained, an alignment is made for the captured image P1 using the sectional images P1* on the side closer to the rotating table 5. However, the sectional images P3* may be aligned with each other in a similar manner to obtain a captured image P3. Yet, because of deflection or flexure that can occur in the sidewall, the sectional images P3* may sometimes fail to maintain constancy in the circumferential direction. It is preferable, therefore, that the sectional images P1* on the side closer to the rotating table 5 are used for the alignment.

Also, the alignment may be performed for the sectional images P2*, which constitute a captured image P2 of the inside surface of the tire crown T2. More specifically, an arc along the sectional shape of the tire crown T2 is set by setting the top position, or the farthest point from the camera 12B, of the tire crown T2 in the sectional images P2* as the extremal value and selecting an arc point from each of the range of 20 to 80 pixels above and below the extremal value. Then the center position of the arc in each of the sectional images P2* is calculated, an approximate curve of a broken line connecting the center positions in the sectional images P2* is obtained by performing a Fourier transform on the broken line, and the sectional images P2* of the tire crown T2 can be aligned with each other by shifting the center positions onto the approximate curve.

Since at least two extremal values can be obtained in the maximum width portion of the tire, arcs containing the two extremal values can be set in each of the sectional images.

In the foregoing specification, the invention has been described with reference to specific embodiments thereof. It will, however, be evident that various modifications and changes may be made thereto without departing from the broader spirit and scope of the invention.

What is claimed is:

1. An image processing apparatus for tire appearance inspection comprising:
   a table that is configured to hold a tire to be inspected;
   a plurality of cameras positioned within an inner opening area of the tire and configured to capture images of an inside surface of a sidewall of the tire; and
   a processor configured to:
      control the plurality of cameras to acquire images such that each of the images includes a cross-sectional shape of the inside surface of the sidewall of the tire in a tire radial direction along a circumference of the tire, the inside surface of the tire sidewall including a bead, wherein the plurality of cameras are controlled such that, for each of the cross-sectional shapes, data from the acquired images includes the following information, which is then extracted:
  a bead-side extremal value and a sidewall-side extremal value;
  a bead-side arc point selected from positions 20 to 80 pixels on a curve leftward from the bead-side extremal value and another bead-side arc point selected from positions 20 to 80 pixels on a curve rightward from the bead-side extremal value; and
  a sidewall-side arc point selected from the positions 20 to 80 pixels on a curve leftward from the sidewall-side extremal value and another sidewall-side arc point selected from the positions 20 to 80 pixels on a curve rightward from the sidewall-side extremal value;
for each of the acquired images:
  set a bead-side arc by calculating the bead-side arc point, the other bead-side arc point and the bead-side extremal value;
  set a sidewall-side arc by calculating the sidewall-side arc point, the other sidewall-side arc point and the sidewall-side extremal value;
  determine a center position of the bead-side arc, the center position of the bead-side arc being an intersection of a normal line from a midpoint of a line segment connecting the bead-side arc point and the bead-side extremal value and a normal line from a midpoint of the line segment connecting the bead-side extremal value and the other bead-side arc point; and
  determine a center position of the sidewall-side arc, the center position of the sidewall-side arc being an intersection of a normal line from a midpoint of a line segment connecting the sidewall-side arc point and the sidewall-side extremal value and a normal line from a midpoint of the line segment connecting the sidewall-side extremal value and the sidewall-side arc point;
calculate a bead-side center curve by performing a Fourier transform on a line connecting the center positions of the bead-side arcs of the cross-sectional shapes in the acquired images;
calculate a sidewall-side center curve by performing a Fourier transform on a line connecting the center positions of the sidewall-side arcs of the cross-sectional shapes in the acquired images; and
generate an enhanced inspection image by aligning each of the acquired images by placing the center positions of the bead-side arcs for the cross-sectional shapes on the bead-side curve and placing the center positions of the sidewall-side arcs on the sidewall-side curve.

2. The image processing apparatus for tire appearance inspection according to claim 1, wherein, in the Fourier transform, a primary component is employed only.

3. The image processing apparatus for tire appearance inspection according to claim 1, wherein the bead-side extremal value is a point where a straight line connecting the inflection point of the cross-sectional shape of the image and the bead-side end point thereof, when parallely moved, touches an upward swelling curve near the bead of the cross-sectional shape.

4. The image processing apparatus for tire appearance inspection according to claim 3, wherein a position where the upward-swelling curve is connected to a downward-swelling curve along the sidewall is the inflection point on the respective cross-sectional shape.

5. The image processing apparatus for tire appearance inspection according to claim 4, the sidewall-side extremal value is the position where a straight line parallel to the coordinate axis in the radial direction, when moved up or down, touches the downward-swelling curve along the sidewall.

6. The image processing apparatus for tire appearance inspection according to claim 1, wherein the processor is further programmed to:
  automatically detect whether or not the tire has any defective spots based on the enhanced inspection image; and
  determine that the tire should be rejected, if defective spots are detected in the enhanced inspection image.

7. An image processing method for tire appearance inspection comprising:
  controlling a plurality of cameras that are: (i) positioned within an inner opening area of a tire to be inspected that is held by a table, and (ii) configured to capture images of an inside surface of a sidewall of the tire, wherein the plurality of cameras are controlled to acquire images such that each of the images includes a cross-sectional shape of the inside surface of the sidewall of the tire in tire radial direction along a circumference of the tire, the inside surface of the tire sidewall including a bead, and the plurality of cameras are controlled such that, for each of the cross-sectional shapes, data from the acquired images includes the following information, which is then extracted:
    a bead-side extremal value and a sidewall-side extremal value;
    a bead-side arc point selected from positions 20 to 80 pixels on a curve leftward from the bead-side extremal value and another bead-side arc point selected from positions 20 to 80 pixels on a curve rightward from the bead-side extremal value; and
    a sidewall-side arc point selected from positions 20 to 80 pixels on a curve leftward from the sidewall-side extremal value and another sidewall-side arc point selected from positions 20 to 80 pixels on a curve rightward from the sidewall-side extremal value;
  for each of the acquired images:
    setting a bead-side arc by calculating the bead-side arc point, the other bead-side arc point and the bead-side extremal value;
    setting a sidewall-side arc by calculating the sidewall-side arc point, the other sidewall-side arc point and the sidewall-side extremal value;
    determining a center position of the bead-side arc, the center position of the bead-side arc being an intersection of a normal line from a midpoint of a line segment connecting the bead-side arc point and the bead-side extremal value and a normal line from a midpoint of the line segment connecting the bead-side extremal value and the other bead-side arc point; and
    determining a center position of the sidewall-side arc, the center position of the sidewall-side arc being an intersection of a normal line from a midpoint of a line segment connecting the sidewall-side arc point and the sidewall-side extremal value and a normal line from a midpoint of the line segment connecting the sidewall-side extremal value and the sidewall-side arc point;

calculating a bead-side center curve by performing a Fourier transform on a line connecting the center positions of the bead-side arcs of the cross-sectional shapes in the acquired images;

calculating a sidewall-side center curve by performing a Fourier transform on a line connecting the center positions of the sidewall-side arcs of the cross-sectional shapes in the acquired images; and generating an enhanced inspection image by aligning each of the acquired images by placing the center positions of the bead-side arcs for the cross-sectional shapes on the bead-side curve and placing the center positions of the sidewall-side arcs on the sidewall-side curve.

8. The image processing method apparatus for tire appearance inspection according to claim 7, wherein, in the Fourier transform, a primary component is employed only.

9. The image processing method for tire appearance inspection according to claim 7, further comprising:

automatically detecting whether or not the tire has any defective spots based on the enhanced inspection image; and determining that the tire should be rejected, if defective spots are detected in the enhanced inspection image.

* * * * *